US009873843B2

United States Patent
Nicolosi et al.

(10) Patent No.: US 9,873,843 B2
(45) Date of Patent: Jan. 23, 2018

(54) ONE-POT PROCESS FOR THE PRODUCTION OF BIODIESEL AND GLYCEROL ETHER MIXTURES USEFUL AS BIOFUELS

(71) Applicant: CONSIGLIO NAZIONALE DELLE RICERCHE, Rome (IT)

(72) Inventors: Giovanni Nicolosi, Catania (IT); Carmelo Drago, Catania (IT); Leonarda Francesca Liotta, Catania (IT); Valeria La Parola, Catania (IT); Maria Luisa Testa, Catania (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 54 days.

(21) Appl. No.: 14/765,745

(22) PCT Filed: Feb. 4, 2014

(86) PCT No.: PCT/IB2014/058783
§ 371 (c)(1),
(2) Date: Aug. 4, 2015

(87) PCT Pub. No.: WO2014/122579
PCT Pub. Date: Aug. 14, 2014

(65) Prior Publication Data
US 2016/0024408 A1 Jan. 28, 2016

(30) Foreign Application Priority Data
Feb. 5, 2013 (IT) .............................. MI2013A0156

(51) Int. Cl.
*C10L 1/02* (2006.01)
*B01J 19/10* (2006.01)
(Continued)

(52) U.S. Cl.
CPC ............... *C10L 1/026* (2013.01); *B01J 19/10* (2013.01); *B01J 19/126* (2013.01); *B01J 19/129* (2013.01);
(Continued)

(58) Field of Classification Search
CPC .... C10L 1/026; C10L 1/1852; C10L 2290/34; C10L 2270/026; C10L 2200/0254;
(Continued)

(56) References Cited

U.S. PATENT DOCUMENTS 6,664,404 B2 * 12/2003 Jackson .................. C07C 67/03
554/168
8,052,848 B2 * 11/2011 Kropf ...................... B01J 19/10
204/157.62
(Continued)

FOREIGN PATENT DOCUMENTS

WO 2009/115274 A1 9/2009

OTHER PUBLICATIONS

Vyas A. P. et al.: "A review on FAME production processes", Fuel, IPC Science and Technology Press, Guildford, GB, vol . 89, No. 1, Jan. 1, 2010 (Jan. 1, 2010), pp. 1-9, XP026667954, ISSN: 0016-2361, DOI: 10.1016/J.FUEL.2009.08.014 [retrieved on Aug. 27, 2009] abstract p. 4, paragraph 3.6-p. 7, paragraph 3.7.
(Continued)

*Primary Examiner* — Keith Hendricks
*Assistant Examiner* — Colleen M Raphael
(74) *Attorney, Agent, or Firm* — Young & Thompson

(57) ABSTRACT

A process for the conversion of a feedstock containing one or more fatty acid triglycerides to a mixture containing one or more fatty acid alkyl esters and t-alkyl glycerols, including reacting the feedstock with a compound of formula (I):

R—O—R'     (I)

(Continued)

wherein:

R' is an alkyl, alkenyl or alkynyl having 1-18 carbon atoms;

R is H or a tertiary alkyl group, wherein the reaction takes place in the presence of an acid transesterification catalyst by irradiation with microwaves and/or ultrasound and/or radio waves.

13 Claims, 3 Drawing Sheets

(51) Int. Cl.
    *C07C 67/24*     (2006.01)
    *C07C 41/14*     (2006.01)
    *C11C 3/00*     (2006.01)
    *B01J 19/12*     (2006.01)
    *C07C 41/09*     (2006.01)
    *C07C 67/297*     (2006.01)
    *C10L 1/185*     (2006.01)

(52) U.S. Cl.
    CPC .............. *C07C 41/09* (2013.01); *C07C 41/14* (2013.01); *C07C 67/24* (2013.01); *C07C 67/297* (2013.01); *C10L 1/1852* (2013.01); *C11C 3/003* (2013.01); *C10L 2200/0254* (2013.01); *C10L 2200/0476* (2013.01); *C10L 2270/026* (2013.01); *C10L 2290/34* (2013.01); *C10L 2290/36* (2013.01); *Y02E 50/13* (2013.01)

(58) Field of Classification Search
    CPC ... C10L 2200/01012; C10L 2200/0476; C10L 2290/36; B01J 19/10; B01J 19/126; B01J 19/129; C07C 67/297; C07C 41/09; C07C 41/14; C07C 67/24; C11C 3/003; Y02E 50/13
    USPC .................................................... 204/157.62
    See application file for complete search history.

(56) References Cited

U.S. PATENT DOCUMENTS

| | | | | |
|---|---|---|---|---|
| 8,591,605 | B2* | 11/2013 | Misra | C10L 1/19 |
| | | | | 44/307 |
| 8,858,657 | B1* | 10/2014 | Deng | C10L 1/026 |
| | | | | 435/135 |
| 2005/0274065 | A1* | 12/2005 | Portnoff | C07C 67/08 |
| | | | | 44/605 |
| 2009/0000941 | A1* | 1/2009 | Kropf | B01J 19/10 |
| | | | | 204/157.62 |
| 2009/0148920 | A1* | 6/2009 | Schreck | C07C 67/03 |
| | | | | 435/135 |
| 2009/0234146 | A1* | 9/2009 | Cooney | B01D 11/0288 |
| | | | | 554/174 |
| 2010/0130763 | A1* | 5/2010 | Gao | C07C 67/03 |
| | | | | 554/167 |

OTHER PUBLICATIONS

Zhang S. et al.: "Rapid microwave-assisted transesterification of yellow horn oil to biodiesel using a heteropolyacid solid catalyst", Bioresource Technology, Elsevier BV, GB, vol. 101, No. 3, Feb. 1, 2010 (Feb. 1, 2010), pp. 931-936, XP026698597, ISSN: 0960-8524, DOI: 10.1016/J.BIORTECH.2009.08.069 [retrieved on Sep. 29, 2009] abstract.

International Search Report, dated Apr. 3, 2014, from corresponding PCT application.

Melero et al., "Advances in the Synthesis and Catalytic Applications of Organosulfonic-Functionalized Mesostructured Materials," Chem. Rev., Mar. 6, 2006, vol. 106, No. 9, pp. 3790-3812, Spain.

Melero et al., "Acid-Catalyzed Etherification of Bio-Glycerol and Isobutylene Over Sulfonic Mesostructured Silicas," Applied Catalysis A: General, 346, Apr. 30, 2008, pp. 44-51, Spain.

Frusteri et al., "Catalytic Etherification of Glycerol by Tert-Butyl Alcohol to Produce Oxygenated Additives for Diesel Fuel," Applied Catalysis A: General, 367, Jul. 24, 2009, pp. 77-83, Spain.

\* cited by examiner

ONE-POT PROCESS FOR THE PRODUCTION OF BIODIESEL AND GLYCEROL ETHER MIXTURES USEFUL AS BIOFUELS

The present invention relates to a "one-pot" process for the conversion of oils and fats of various origins to mixtures containing fatty acid methyl esters and tert-butyl glycerols, which are useful as biofuels.

Biodiesel is a non-toxic, biodegradable alternative fuel obtained from renewable sources. The exhaust gases deriving from biodiesel combustion do not contain sulphur, and contain a lower quantity of particulate matter than conventional diesel; biodiesel is therefore an excellent alternative to fossil fuels with a view to reducing greenhouse gas emissions. Biodiesel is a mixture of fatty acid methyl esters (FAME) obtained from the transesterification reaction of vegetable oils, mainly triglycerides, with methanol, in the presence of acid, basic or enzymatic catalysis.

The transesterification reaction with an alcohol leads to the formation of FAME and glycerin. The glycerin produced by the reaction must be removed from the reaction mixture or recovered by a further conversion. The production of glycerin therefore has a considerable effect on the economy of the process.

Glycerol is used in the synthesis of acrolein, propylene glycol, 1,3-propanediol, glyceric acid and glycerol carbonate. However, in view of the enormous amount of glycerol produced nowadays, the most convenient use may be to convert it to fuel additives. For that purpose, in order to make glycerol volatile, direct acetylation processes catalysed by Amberlyst-15®, mesostructured silica functionalised with sulphonic groups, and hydroxylated magnesium fluorides, have been developed to obtain triacetin in a satisfactory manner. However, the etherification of glycerol remains the best solution for the production of additives for both internal combustion and diesel engines. In particular, glycerol tert-butyl ethers (GTBE) are the most widely used today, the most convenient being diethers, because monoethers are less soluble in normal fuels, while triethers are not particularly economical due to the high isobutene content required for their preparation.

In the synthesis of GTBE, carried out using isobutene or t-butanol as reagent, the acidity of the catalyst is crucial, and catalysts such as sulphuric acid or mesostructured silica functionalised with sulphonic groups have been studied in this context (J. A. Melero et al. Advances in the Synthesis and Catalytic Applications of Organosulfonic-Functionalized Mesostructured Materials. *Chem. Rev.*, 106, 2006, 3790; J. A. Melero et al., Acid-catalyzed etherification of bio-glycerol and isobutylene over sulfonic mesostructured silicas. *Appl. Catal. A-Gen.*, 346 (2008) 44-51; F. Frusteri et al., Catalytic etherification of glycerol by tert-butyl alcohol to produce oxygenated additives for diesel fuel. *Appl. Catal. A: Gen.*, 367 (2009), 77-83).

Patent application WO2009/115274 discloses a process for the production of biodiesel which comprises the reaction of a mixture of biological origin containing fatty acid triglycerides with methyl-t-butyl-ether, in the presence of an acid catalyst, to give a mixture containing fatty acid methyl esters and t-butyl glycerols. The reaction is conducted in two stages at different temperatures; the first at a temperature ranging between 120° and 150° C. for 2-3 hours, and the second at a temperature ranging between 50° and 100° C. for 5-6 hours (p. 8, lines 1-9). The examples demonstrate that the conversion of glycerin to ethers is between 30 and 40%, and the unreacted glycerin must therefore be separated from the final reaction mixture.

It has now been found that by irradiating a reaction mixture containing fatty acid triglycerides and methyl-t-butyl-ether in the presence of an acid catalyst with electromagnetic waves such as microwaves, ultrasound and/or radio waves, almost total conversion to fatty acid methyl esters and t-butyl glycerols is obtained without glycerin formation. The reaction times are also considerably reduced. This process therefore offers considerable advantages from the industrial standpoint, because it eliminates the final stage of glycerin separation, and energy consumption is lower than in the known processes.

It has also been observed that the conversion proceeds efficiently with oils containing large amounts of free fatty acids, which usually limit the use of conventional industrial processes for biodiesel production, unless the oils are pretreated to remove them. This advantage confirms the versatility of the process, allowing the use of inedible and waste vegetable oils containing amounts of free fatty acids, such as exhausted frying oils from the catering industry. The object of the present invention is a process for the conversion of a feedstock containing one or more fatty acid triglycerides to a mixture containing one or more fatty acid alkyl esters and t-alkyl glycerols, comprising the reaction of said feedstock with a compound of formula (I):

$$R-O-R^I \qquad (I)$$

wherein:

$R^I$ is an alkyl, alkenyl or alkynyl having 1-18 carbon atoms;

R is H or a tertiary alkyl group of formula (II):

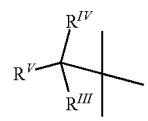

(II)

wherein $R^{III}$, $R^{IV}$ and $R^V$ are independently a straight or branched alkyl, alkenyl or alkynyl group having 1 to 6 carbon atoms;

wherein said reaction takes place in the presence of an acid transesterification catalyst by irradiation with microwaves and/or ultrasound and/or radio waves, provided that when R is H, an alcohol of formula R—OH is added wherein R is as defined above in an equimolar quantity to $R^I$—OH.

$R^{III}$, $R^{IV}$ and $R^V$ are preferably selected from the group consisting of methyl, ethyl, propyl, isopropyl, butyl, t-butyl, ethenyl, propenyl, isopropenyl, butenyl, isobutenyl, hexenyl, ethynyl, propynyl and butynyl. $R^{III}$, $R^{IV}$ and $R^V$ are more preferably methyl.

R is preferably t-butyl.

$R^I$ is preferably a methyl, ethyl, propyl, isopropyl or butyl. $R^I$ is more preferably methyl.

The reaction is schematically illustrated in

R and $R^I$ are as defined above.

$R^{II}$ is a saturated or unsaturated acyl group, present in the glyceric structure in a structurally homogenous or heterogeneous way, so as to constitute tripalmitin or palm oil, for example.

When $R^I$ is H, an equal quantity of $R^I$—OH alcohol must be added.

In the specific case wherein biodiesel is to be obtained as a final mixture, the triglyceride can be one of the vegetable oils commonly used in the production of biodiesel, and t-butyl methyl ether can be used as ether. If the corresponding t-butyl alcohol is used instead of t-butyl ether, an equal quantity of methanol must be added.

The feedstock containing one or more fatty acid triglycerides can contain:
vegetable oils, such as those selected from the following group:
coconut oil, corn oil, cottonseed oil, olive oil, palm oil, peanut oil, rapeseed oil, canola oil, safflower oil, sesame oil, soybean oil, sunflower oil, almond oil, beechnut oil, cashew oil, hazelnut oil, macadamia oil, pine nut oil, pistachio oil, walnut oil, citrus oils, grapefruit seed oil, lemon oil, orange oil, castor oil, hemp oil, mustard oil, radish oil, rice bran oil, salicornia oil, jatropha oil, jojoba oil, linseed oil, poppy oil, stillingia oil, fruit tree oil, artichoke oil, carrot seed oil, mango oil and sea-buckthorn oil;
animal fats, such as those selected from the following group: beef tallow, lard, poultry fat and fish oils;
waste oils and fats of various origins, such as those selected from the following group: oils and fats used in restaurants and the catering industry in general, present in waste from the agrifood and fish industries, etc.

The acid catalysts, free or immobilised on a support, are preferably selected from the following group:
strong mineral acids, such as $H_2SO_4$, $HNO_3$, HCl and HF, and organic acids, such as $CH_3COOH$, p-toluenesulphonic acid and derivatives, alkyl sulphonic acids and derivatives;
zeolites, molecular sieves, phosphates, zirconates, kaolinite, montmorillonite, pillared clays, hydrotalcites, and acid ion-exchange resins;
solid acid or suitably acid-functionalised materials such as perfluorinated oxides and/or polymers, silicas and silicas doped with Al, Ti or Zr, in different morphologies such as amorphous and mesostructured, heteropolyacids adsorbed and/or covalently bonded to metal oxides; metal oxides, such as $Al_2O_3$ and $ZrO_2$, functionalised with phosphate and/or sulphate groups; organic sulphonic and/or organic carboxylic acids immobilised on amorphous silica and/or meso- and microstructured silica; polyoxymetalates stabilised on silica and/or titania; Keggin structures containing niobium ions, ionic liquids and/or carbon nanotubes (single and multiwalled) functionalised with organic sulphonic and/or organic carboxylic acids.

Irradiation can take place at microwave, ultrasound or radio wave electromagnetic frequencies or at different types of electromagnetic frequencies, simultaneously or in succession.

"Microwaves" means electromagnetic radiation with a frequency ranging from 0.3 to 300 GHz; microwaves with a frequency ranging from 0.9 to 25 GHz, and in particular from 2 to 3 GHz, are preferably used.

"Ultrasound" means mechanical sound waves with a frequency exceeding 20 KHz; radiation with a frequency ranging between 20 and 100 KHz is preferably used.

"Radio waves" means electromagnetic radiation with a frequency ranging from 0 to 300 GHz; radio waves with a frequency ranging from 1 to 100 MHz, more preferably from 10 to 50 MHz, are preferably used.

The reaction mixture is preferably irradiated for between 0.15 and 3-4 hours.

The acid catalyst used in the reaction can be a free acid catalyst or immobilised on a support.

The acid catalyst is preferably selected from the group consisting of:

strong mineral acids, such as $H_2SO_4$, $HNO_3$, HCl and HF, and organic acids, such as $CH_3COOH$, p-toluenesulphonic acid and derivatives, alkyl sulphonic acids and derivatives;
zeolites, such as ZSM-5, mordenite, Y, USY and beta zeolites, SAPO-11, SAPO-34, molecular sieves, phosphates, zirconates, kaolinite, montmorillonite, pillared clays, hydrotalcites, and acid ion-exchange resins such as Amberlyst-15®, and -35®, Nafion SAC-13®, etc.;
solid acid or suitably acid-functionalised materials such as perfluorinated oxides and/or polymers like Nafion SAC-13, immobilised on silica; silicas and silicas doped with Al, Ti or Zr in different morphologies such as amorphous xerogel or aerogel, meso- and microstructured, like MCM41, MCM48, SBA-15 and HMS, heteropolyacids (HPAs), acids adsorbed and/or covalently bonded to metal oxides such as $Al_2O_3$ and/or $ZrO_2$ oxides functionalised with phosphate and/or sulphate groups; organic sulphonic and/or organic carboxylic acids immobilised on amorphous silica and/or meso- and microstructured silica; polyoxymetalates stabilised on silica and/or titania; Keggin structures containing niobium ions; niobium oxides; ionic liquids and/or carbon nanotubes (single and multiwalled) functionalised with organic sulphonic and/or organic carboxylic acid.

EXAMPLES

Example 1

Figure 1:
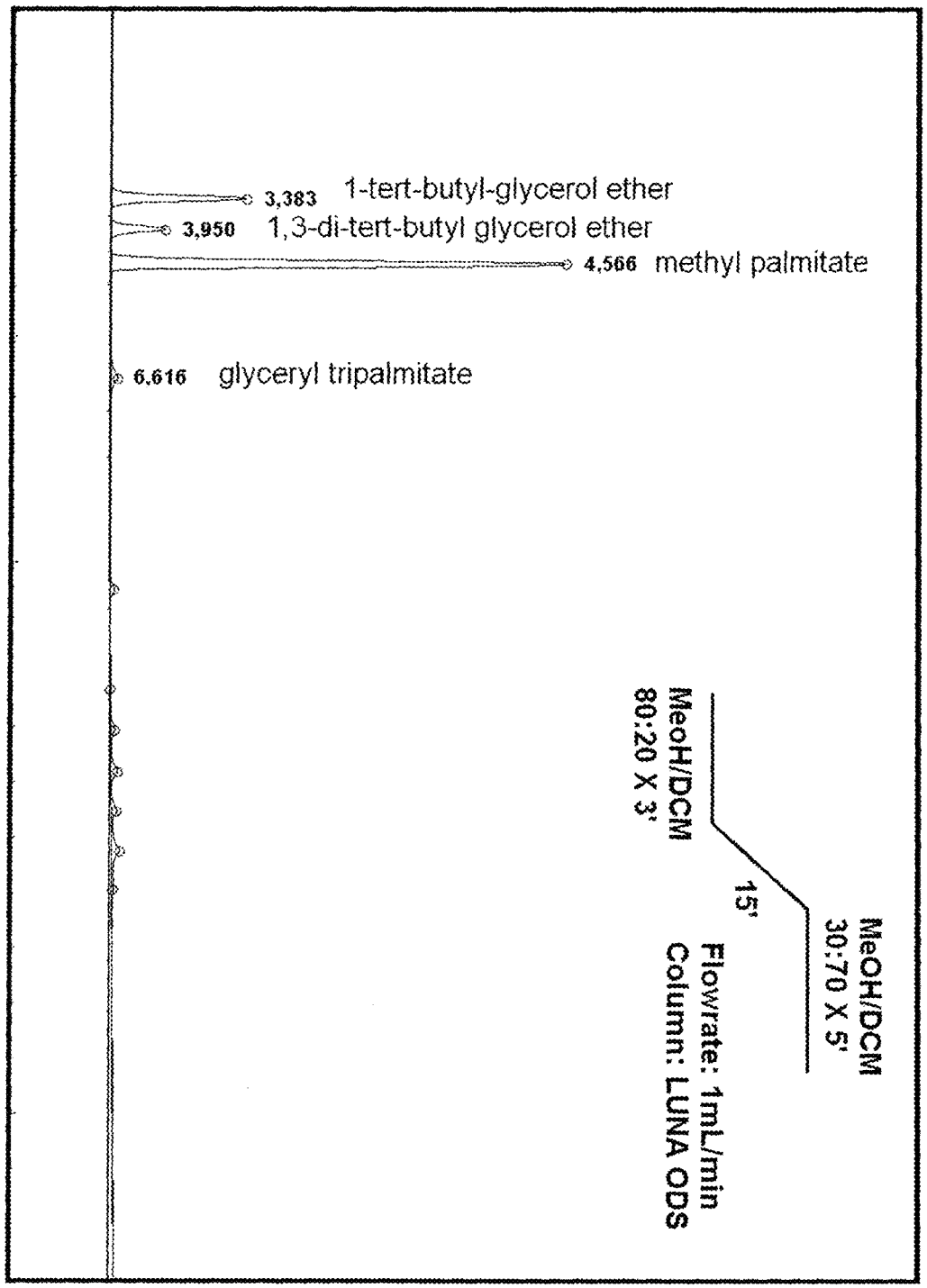
FIG. 1: HPLC analysis of the reaction mixture of Example 1

Conversion of Tripalmitin to a Mixture of Methyl Palmitate and Glycerol Tert-Butyl Ethers 500 mg of glycerol tripalmitate (MW 807.32, 0.619 mmol), dissolved in 1.6 ml of tert-butyl-methyl ether (d 0.744 mg/ml, MW 88.15, 24.5 mmol), is placed in a microwave test tube, and 30 mg of catalyst, consisting of amorphous silica 10% functionalised with sulphonic groups, is added to the solution. The reaction mixture is irradiated by 20 watt microwaves, under stirring, for a reaction time of up to 3 hours. The HPLC assay demonstrates the almost total conversion of glycerol tripalmitate to methyl palmitate and a mixture of mono- and di-tert-butyl glycerol ethers, in a 70:30 ratio. There is no formation of free glycerol, as shown in FIG. 1.

Example 2

Figure 2:
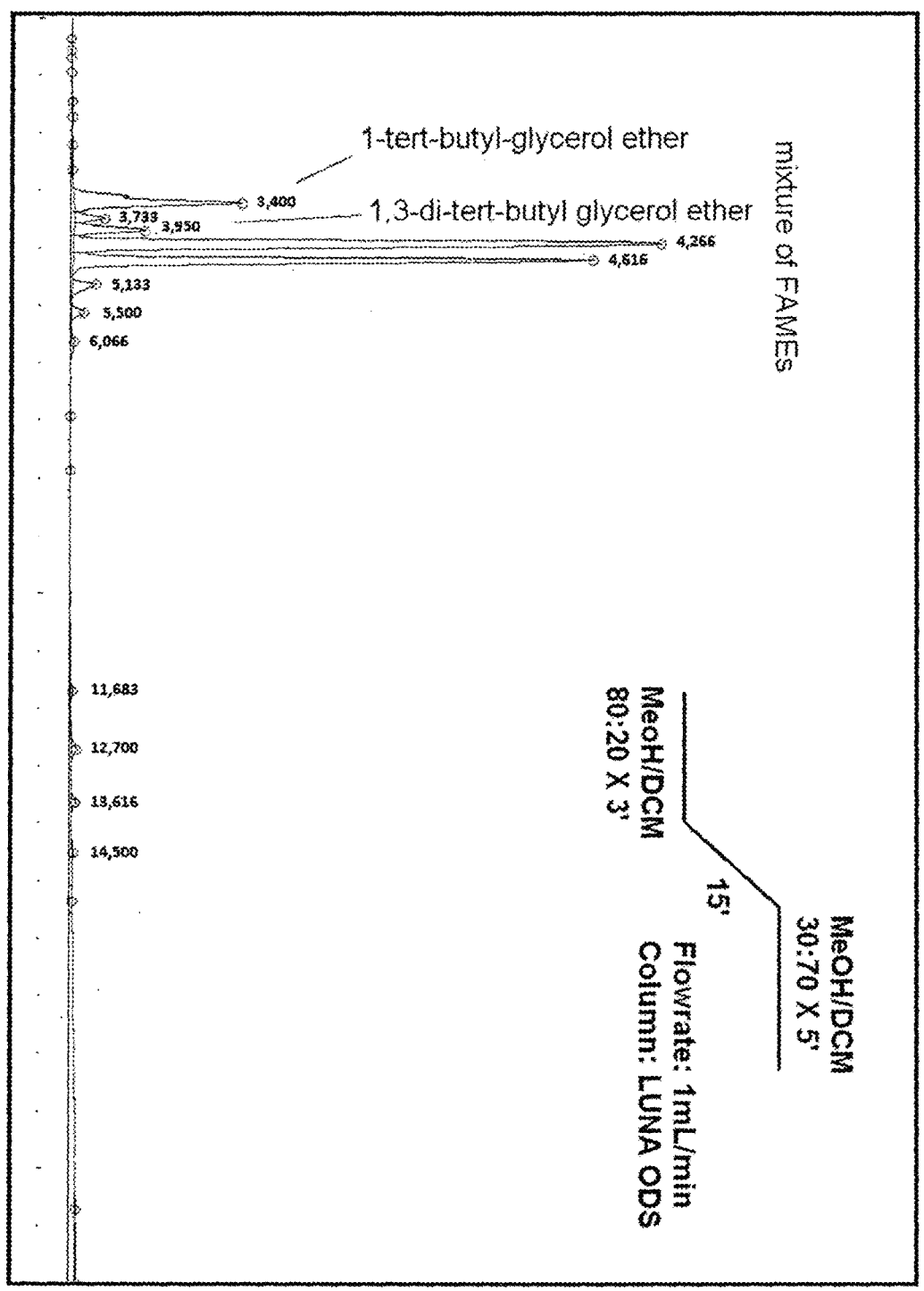
FIG. 2: HPLC analysis of the reaction mixture of Example 2
Figure 3:
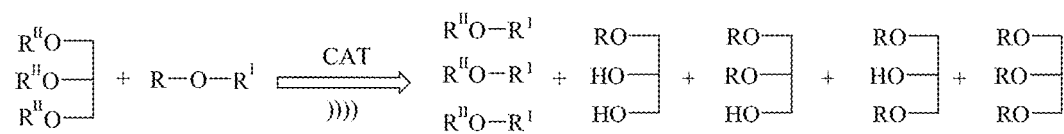
FIG. 3: Schematic illustration of a reaction

Conversion of Soybean Oil to a Mixture of FAMEs and Glycerol Tert-Butyl Ethers 1 g of soybean oil (d 0.917 mg/ml, 0.619 mmol), dissolved in 3.2 ml of tert-butyl-methyl ether (d 0.744 mg/ml, MW 88.15, 24.5 mmol), is placed in a microwave vial, and 30 mg of catalyst, consisting of amorphous silica 10% functionalised with sulphonic groups, is added to the solution. The reaction mixture is irradiated by 20 watt microwaves, under stirring, for a reaction time of up to 3 hours. The HPLC assay demonstrates the almost total conversion of soybean oil to a mixture of fatty acid methyl esters, FAME, mono- and di-tert-butyl glycerol ethers, the latter in a 70:30 ratio. There is no formation of free glycerol, as shown in FIG. 2.

The invention claimed is:

1. A process for converting a feedstock containing one or more triglycerides of fatty acids to a mixture containing one or more alkyl esters of fatty acids and t-alkyl glycerols, comprising carrying out a reaction of said feedstock with a compound of formula (I):

wherein:
R$^I$ is an alkyl, alkenyl or alkynyl having 1-18 carbon atoms;
R is H or a tertiary alkyl group of formula (II):

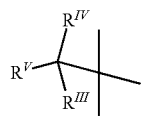

wherein R$^{III}$, R$^{IV}$ and R$^V$ are independently a straight or branched alkyl, alkenyl or alkynyl group having 1 to 6 carbon atoms;
wherein said reaction is carried out in the presence of an acid transesterification catalyst by irradiation with microwaves and/or ultrasound and/or radio waves, said reaction produces a mixture containing one or more alkyl esters of fatty acids and t-alkyl glycerols, provided that when R is H in the compound of formula (I), an alcohol of formula R—OH is added, wherein R is the tertiary alkyl group of formula (II) as defined above, in an equimolar amount to R$^I$—OH.

2. The process according to claim 1, wherein R$^{III}$, R$^{IV}$ and R$^V$ in formula (II) are selected from the group consisting of methyl, ethyl, propyl, isopropyl, butyl, t-butyl, ethenyl, propenyl, isopropenyl, butenyl, isobutenyl, hexenyl, ethynyl, propynyl and butynyl.

3. The process according to claim 2, wherein R$^{III}$, R$^{IV}$ and R$^V$ in formula (II) are methyl.

4. The process according to claim 2, wherein R$^I$ in formula (I) is selected from the group consisting of methyl, ethyl, propyl, isopropyl and butyl.

5. The process according to claim 3, wherein R$^I$ in formula (I) is selected from the group consisting of methyl, ethyl, propyl, isopropyl and butyl.

6. The process according to claim 1, wherein R$^I$ in formula (I) is selected from the group consisting of methyl, ethyl, propyl, isopropyl and butyl.

7. The process according to claim 6, wherein R$^I$ in formula (I) is methyl.

8. The process according to claim 1, wherein the compound of formula (I) is tert-butyl methyl ether.

9. The process according to claim 1, wherein the feedstock is selected from the group consisting of:
vegetable oils selected from the group consisting of coconut oil, corn oil, cottonseed oil, olive oil, palm oil, peanut oil, rapeseed oil, canola oil, safflower oil, sesame oil, soybean oil, sunflower oil, almond oil, beech nut oil, cashew oil, hazelnut oil, macadamia oil, pine nut oil, pistachio oil, walnut oil, citrus oils, grapefruit seed oil, lemon oil, orange oil, castor oil, hemp oil, mustard oil, radish oil, rice bran oil, salicornia oil, soybean oil, jatropha oil, jojoba oil, linseed oil, poppy oil, stillingia oil, fruit tree oil, artichoke oil, carrot seed oil, mango oil and sea-buckthorn oil;
animal fats selected from the group consisting of beef tallow, lard, poultry fat and fish oils;
waste oils and fats from an industry selected from the group consisting of restaurants, catering, agrifood, and seafood.

10. The method according to claim 1, wherein irradiation takes place with only one type of electromagnetic frequency selected from the group consisting of microwaves, ultrasound and radio waves or with different types of said electromagnetic frequency, simultaneously or in succession.

11. The method according to claim 1, wherein the acid catalyst used in the reaction may be a free acid catalyst or immobilised on a support.

12. The process according to claim 11, wherein the acid catalyst is selected from the group consisting of:
strong mineral acids and organic acids;
zeolites, molecular sieves, phosphates, zirconates, kaolinite, montmorillonite, pillared clays, hydrotalcites and acid ion-exchange resins;
solid acid or acid-functionalised materials selected from the group consisting of perfluorinated oxides, polymers and combinations thereof; silicas and silicas doped with Al, Ti or Zr in different morphologies, heteropolyacids, acids adsorbed and/or covalently bonded to metal oxides;
organic sulphonic and/or organic carboxylic acids immobilised on amorphous silica and/or meso- and microstructured silica;
polyoxymetalates stabilised on silica and/or titania;
Keggin structures containing niobium ions;
niobium oxides; and
ionic liquids and/or carbon nanotubes functionalised with organic sulphonic acids and/or organic carboxylic acids.

13. The process according to claim 12, wherein the acid catalyst is alkylsulphonic acid bound to amorphous silica.

* * * * *